US010568580B2

(12) United States Patent
Morger (10) Patent No.: US 10,568,580 B2
(45) Date of Patent: Feb. 25, 2020

(54) PERSON BED HAVING A SENSING APPARATUS FOR BODY STATICS FOR IMAGING MEDICAL EXAMINATION DEVICES (71) Applicant: STYFOLOGIE-CENTER GMBH, Rapperswil (CH)

(72) Inventor: Otto Morger, Rapperswil (CH)

(73) Assignee: STYFOLOGIE-CENTER GMBH (CH)

( * ) Notice: Subject to any disclaimer, the term of this patent is extended or adjusted under 35 U.S.C. 154(b) by 181 days.

(21) Appl. No.: 15/526,756

(22) PCT Filed: Nov. 13, 2015

(86) PCT No.: PCT/IB2015/058771
§ 371 (c)(1),
(2) Date: May 13, 2017

(87) PCT Pub. No.: WO2016/075659
PCT Pub. Date: May 19, 2016

(65) Prior Publication Data
US 2017/0311896 A1 Nov. 2, 2017

(30) Foreign Application Priority Data

Nov. 13, 2014 (CH) .................................. 01764/14

(51) Int. Cl.
*A61B 6/03* (2006.01)
*A61B 5/00* (2006.01)
(Continued)

(52) U.S. Cl.
CPC .............. *A61B 5/70* (2013.01); *A61B 5/0033* (2013.01); *A61B 5/0064* (2013.01);
(Continued)

(58) Field of Classification Search
CPC ... A61B 5/0033; A61B 5/0064; A61B 5/0555; A61B 5/1079; A61B 5/70; A61B 6/04
See application file for complete search history.

(56) References Cited

U.S. PATENT DOCUMENTS

2003/0083562 A1* 5/2003 Bani-Hashemi ..... A61B 5/0064
600/407
2004/0186374 A1* 9/2004 Satragno ................ A61B 5/055
600/415
(Continued)

FOREIGN PATENT DOCUMENTS

DE        3629801 A1    3/1988
DE       69514625 T2    8/2000
DE    102011083876 A1    4/2013

OTHER PUBLICATIONS

International Search Report; PCT Application No. PCT/IB2015/058771; dated Feb. 29, 2016.
(Continued)

*Primary Examiner* — Puya Agahi
(74) *Attorney, Agent, or Firm* — Polsinelli PC (57) ABSTRACT The patient couch serves for carrying out radiological medical imaging examinations by X-ray, tomography, nuclear magnetic resonance and other imaging methods. The person rests thereon in lying position for the creation of tomographic and other images. The patient couch is equipped with a capturing device, for measuring the patient's body or certain sites of the patient's body by optical, laser-optical, mechanical or electromechanical methods and/or devices. The couch has footrests for positioning the soles of the feet as when standing on vertical supporting faces with natural spreading of the feet, as well as portions for capturing at least the positions of the knee joints, the hip joint, the pelvic bone, the shoulders and the head. Further, the couch is equipped with pressure sensors for measuring the local supported weights of the various supported body sites, for reproducibly capturing the position of the skeleton with regard to its center axis as well as any rotations of shoulder and/or hip.

9 Claims, 7 Drawing Sheets (51) Int. Cl.
*A61B 5/055* (2006.01)
*A61B 5/103* (2006.01)
*A61B 5/107* (2006.01)
*A61B 6/04* (2006.01)

(52) U.S. Cl.
CPC .......... *A61B 5/0555* (2013.01); *A61B 5/1036* (2013.01); *A61B 5/1072* (2013.01); *A61B 5/1079* (2013.01); *A61B 6/032* (2013.01); *A61B 6/0407* (2013.01); *A61B 6/0492* (2013.01)

(56) References Cited

U.S. PATENT DOCUMENTS

2008/0169931 A1* 7/2008 Gentry .................. A61B 5/1113
340/573.1

2015/0272505 A1* 10/2015 Schmidt ................ A61B 6/032
600/407

OTHER PUBLICATIONS

Written Opinion of PCT Application No. PCT/IB2015/058771; dated Feb. 29, 2016.
Robert Grimm, et al. "Markerless Estimation of Patient Orientation, Posture and Pose Using Range and Pressure Imaging; For Automatic Patient Setup and Scanner Initialization in Tomographic Imaging" Obtained on May 4, 2017.
English Language Abstract of DE3629801 Obtained From www.espacenet.com on May 4, 2017.
English Language Abstract of DE69514625 Obtained From www.espacenet.com on May 4, 2017.
English Language Abstract of DE102011083876 Obtained From www.espacenet.com on May 4, 2017.
English Translation of International Search Report; PCT Application No. PCT/IB2015/058771; dated Feb. 29, 2016.

* cited by examiner

PERSON BED HAVING A SENSING APPARATUS FOR BODY STATICS FOR IMAGING MEDICAL EXAMINATION DEVICES

This invention relates to a patient couch for measuring the human body in lying position for carrying out radiological medical imaging examinations by means of X-ray, tomography, nuclear magnetic resonance and other imaging methods for holistically capturing the body statics in lying position, specifically for capturing the position of the skeleton with regard to its center axis as well as any rotations of shoulder and/or hip.

Using imaging methods in medical diagnostics, representations are established of the structure and function of the tissues and organs in the body. For this purpose, in particular procedures of nuclear magnetic resonance (such as MRI—Magnetic Resonance Imaging) or ultrasound are used. X-ray diagnostics is also a widespread imaging method for ascertaining anomalies in the body by the fact that body tissue of different density absorbs the X-rays to different extents, which can be represented correspondingly. In computer tomography (CT), the radiographic images are processed electronically, which gives such images an even substantially higher image quality. Other procedures draw upon radionuclide techniques, infrared radiation, impedance or visible light for capturing body image data.

Information which cannot be provided by one of the above-mentioned apparatus-based examination methods is information about body statics. Without this information there always remains an uncertainty as to whether the images reflect only a momentary body situation. Variations of the body situation seriously affect the overall picture, however. Stress situations or pain of the patient leads to different muscular tensions and therefore to avoidance postures, which would be best measured on the skeleton itself. Such tensions can build up over a long time, yet also occur acutely, so that every stress situation and every perception of pain shows an individual tension pattern. Relevant for the assessment is a knowledge of the causes of the deviations in the imaged position from the normal position, otherwise this can lead to erroneous conclusions.

If information about body statics is missing in the image recordings, the deviations from the normal state are firstly not identifiable and secondly not properly assessable. And thirdly, a new image recording after a therapy cannot be interpreted correctly because both qualitative and quantitative comparisons with the earlier image are not, or only very insufficiently, possible. After a therapy, the patient may be lying on the couch with substantially different body statics and hence the new image then also shows a changed situation, which is not, or not sufficiently well, comparable due to an image recorded with different body statics. Hence, the expensively recorded images are interpreted with very insufficient quality and do not allow a quantitative capture of the changes in body statics at all.

The different leverage forces arising from the tensions in the interior of the body change the skeletal bones, joints and vertebral positions and likewise affect the organs. A skeleton is inherently unstable, so that the false tensions of the muscles move and distort the skeleton with its bones, joints and vertebral bodies. As an example, an MRI or CT picture always shows only the resultant of the tensions. Medical diagnostics is done without collecting body measurement data, so that statics deviations are recognized at best indirectly and only insufficiently in the resulting image. To pursue the cause of the tensions, however, the tension would first have to be exactly measured and its extent determined. The latter would be highly advisable in particular before complicated, irreversible procedures, in order for the cause of the tension, or what is recognized as defective in the MRI, CT, ultrasound or similar images, to be addressed. Because of the non-holistic information about the clinical picture, symptomatic pictures often serve as a basis for operative procedures which could possibly have been prevented by specifically fighting the cause. Or else, even false therapies are prescribed, which combat only the symptoms instead of the causes, and the causes of a complication in the patient thus remain untreated and unresolved.

A common example is the diagnosis of hip joint attrition or so-called hip osteoarthritis. The patient suffers from strong pain due to the attrition of the cartilage surface of socket and femoral head. All too often such a hip joint is replaced partly or even completely by an artificial joint without probing the exact cause for the osteoarthritis. The reason for the attrition, however, is often pelvic obliquity, which results in decades of one-sided attrition of the hip joint. This involves the cartilage between socket and femoral head being overloaded and greatly worn out, which ultimately causes the osteoarthritis. Such causes of a one-sided attrition are unfortunately disregarded. This can be compared to the one-sided wear of an automobile tire, when only the tire is replaced but the cause, the misaligned steering geometry, is not discovered by measurement and corrected. Implanting an unnecessary endoprosthesis, i.e. a replacement part foreign to the body, always means subjecting the patient to unnecessary risks, not to mention the costs for health services. Inserting an artificial hip joint involves the risks of a medium serious operative procedure. Among the most frequently occurring complications of such a procedure are thromboses, infections, postoperative hematomas, afterbleeding or also injuries to nerves and blood vessels. Blood losses can also occur during surgery, making it necessary to supply the patient with autologous or allogeneic blood. There is also the possibility of an implant allergy, in which the patient's body reacts allergically to components of the endoprosthesis, which necessitates revision surgery as when infections arise. Therefore, inserting an endoprosthesis should be considered as the last resort when targeted, cause-fighting therapeutic treatments of hip osteoarthritis have failed.

Investigating the cause is usually complex because the causes of pain and problems in a certain body region not infrequently lie elsewhere, or are triggered in quite another body region. Without information through body-static data, it is practically hopeless to look for the cause detached from the focus of the pain or inflammation. However, these causes are indicated by often slight deflections, dislocations, obliquities, etc., of the skeleton. For a careful diagnosis one therefore has no choice but to assess the data of the imaging methods taking into account this body-statics measurement data.

An apparatus is known from EP 1 408 833 B1 for measuring the human body in upright, standing posture. The person to be measured stands in his or her natural posture on two mutually detached scales, with the left foot on one scales and the right one on the other. These two scales form the lowermost part of the approximately man-high measuring apparatus. Thereabove is located the framework on which the displaceable measuring rods for measuring the body are arranged. Starting out from the false stance arising from the difference of the scales' displays for a pre-specified yet naturally assumable foot position, one mechanically measures lateral hip deviations, lateral deviations of the upper body, rotations, knee position angles, knee extension deficits, hollow back, raised shoulders, etc. In so doing, calibrated measuring rods are manually moved toward the corresponding body points up to a standstill as a result of the body's resistance. At the stop the displayed measurement number is taken down. The measuring rods can be displaced both horizontally and vertically, to account for different body masses. It is thus possible to capture deviations in statics for the entire body reproducibly and exactly.

One problem with such an apparatus is that the measurement of the body can only be done on a standing person. In addition, the measuring procedure is time-consuming, as the respective measuring rod must be advanced manually at each point and the measurement number taken down individually. As a rule this takes about 10 to 20 minutes. When diagnostic examinations are carried out on a patient in the hospital, this involves great effort on the part of the examining doctors as well as the assisting staff, so that even for only half-hour examinations one often has to accept hours-long waiting times. For a measurement of the body by means of an apparatus from EP 1 408 833 B1 as described, additional time must even be planned for, which is practically unviable in view of the tight examination schedule.

Measurement on an apparatus as described will not infrequently give a falsified picture of the person to be measured, because the latter will hardly stand in a natural manner in this special situation. When the person concentrates on his or her natural posture, he or she will unconsciously stretch or tense up in various places. In addition, it is impossible for the person to be measured to always hold the same posture for a quarter of an hour. Inevitably there will be subtle changes in posture. A picture thus obtained will therefore always involve errors.

Patients who must undergo imaging methods like MRI, CT, ultrasound, etc., are often ill and suffer from pain, so that they are restricted in their mobility. In such a case a person cannot be expected to endure a measurement of his or her body lasting a quarter of an hour or longer while standing. For the above-mentioned imaging methods, and sometimes also for X-rays, however, patients can remain in lying position during the entire image recording operation. This also contributes to relaxing them.

The most exact relation between the body measurement data and the image information of an imaging method results from establishing them simultaneously. Then, for example, an MRI image of a certain body part corresponds to the measurement data most exactly when the image recording and the measurement were done in the same body attitude of the respective person. Therefore, the causal connection between ailment and cause is to be inferred from the picture drawn by both sources. On the basis of currently existing measurement possibilities and the possible deviations and avoidance postures which lead to faulty loading and defective functions, there are an immense number of constellations of avoidance postures which inevitably have repercussions over time. This is why the body should be measured in context for an imaging analysis. According to science, every fingerprint is unique and, similarly, avoidance postures are also individual. Measuring the deviations exactly to the millimeter, the following picture results:

Pelvis up to 5 cm lower left or right yields in 5 mm steps: 21 variants
Lateral hip displacement up to 12 cm in mm steps left or right: 240 variants
Hip rotation up to 5 cm in mm steps left or right: 102 variants
Back positions, flat back, hunched back: 2 variants
Hollow back 0-80 mm: 80 variants
Foot positions: 7 variants
Shoulder, lateral deviation up to 12 cm in mm steps left or right: 240 variants
Shoulder, rotation 8 cm in mm steps left or right: 160 variants
Shoulder, height deviation 6 cm in 5 mm steps left or right: 24 variants
Neck, forward position 0-10 cm in mm steps: 100 variants
Neck, lateral deviation 5 cm in 5 mm steps left or right: 22 variants
Head, forward position 0-10 cm in mm steps: 100 variants
Head, lateral deviation 0-5 cm in 5 mm steps left or right: 22 variants
Sides, perpendicular 8 cm-20 cm in mm steps: 120 variants
Knee, stretching deficit 0-8 cm in mm steps left or right: 160 variants
Leg, deviation from pelvis 0-5 cm in mm steps left or right: 100 variants
Difference in foot load 0-40 kg left or right: 80 variants for possible different measurement variants
Additionally: raised shoulders, shoulders pulled forward, drooping shoulders: plus 3 variants To obtain the total number of possible avoidance positions at this resolution of the data, all variants must be multiplied by each other. The resulting number has 30 zeros!

The object of the invention, bearing in mind the above remarks, is to provide a patient couch having a capturing device for body statics for measuring the three-dimensional position of the body's skeleton on the basis of the position of the feet as they are positioned when standing, with the position and alignment of the joints, the pelvis, the spine, the shoulders and the head when lying, and for capturing the support load of the body at every site, so that asymmetries, obliquities and rotations can be measured quantifiably and inferences can be drawn about local tensions.

As a special feature, the patient couch having said capturing device is to supplement existing imaging methods by a new data dimension, by the information of such image recordings together with the measurement data of the above-mentioned capturing device opening up a comprehensive overall picture of the body and its body statics with regard to the complaint. Said capturing device should be simple in design and usable on a lying patient optionally during an imaging method.

The object of the invention is achieved by a patient couch for carrying out radiological medical imaging examinations by means of X-ray, tomography, nuclear magnetic resonance and other imaging methods in which tomographic and other images of a person in lying position are created, characterized in that the couch is equipped with a capturing device for measuring the patient's body or certain sites of the patient's body by optical, laser-optical, mechanical or electromechanical means, having footrests for positioning the soles of the feet as when standing on vertical supporting faces with natural spreading of the feet, and for capturing at least the positions of the knee joints, the hip joint, the pelvic bone, the shoulders and the head, and that the couch is equipped with pressure sensors for measuring the local supported weights of the various supported body sites, for reproducibly capturing the position of the skeleton with regard to its center axis as well as any rotations of shoulder and/or hip.

Capturing this information and data subsequently enables a targeted therapy, and a new measuring and creating of a corresponding image then allows change to be quantified and the success of a therapy to be correctly assessed and proved.

The invention is represented in the figures on the basis of exemplary embodiments and will be described and explained hereinafter.

There are shown.

Figure 1:
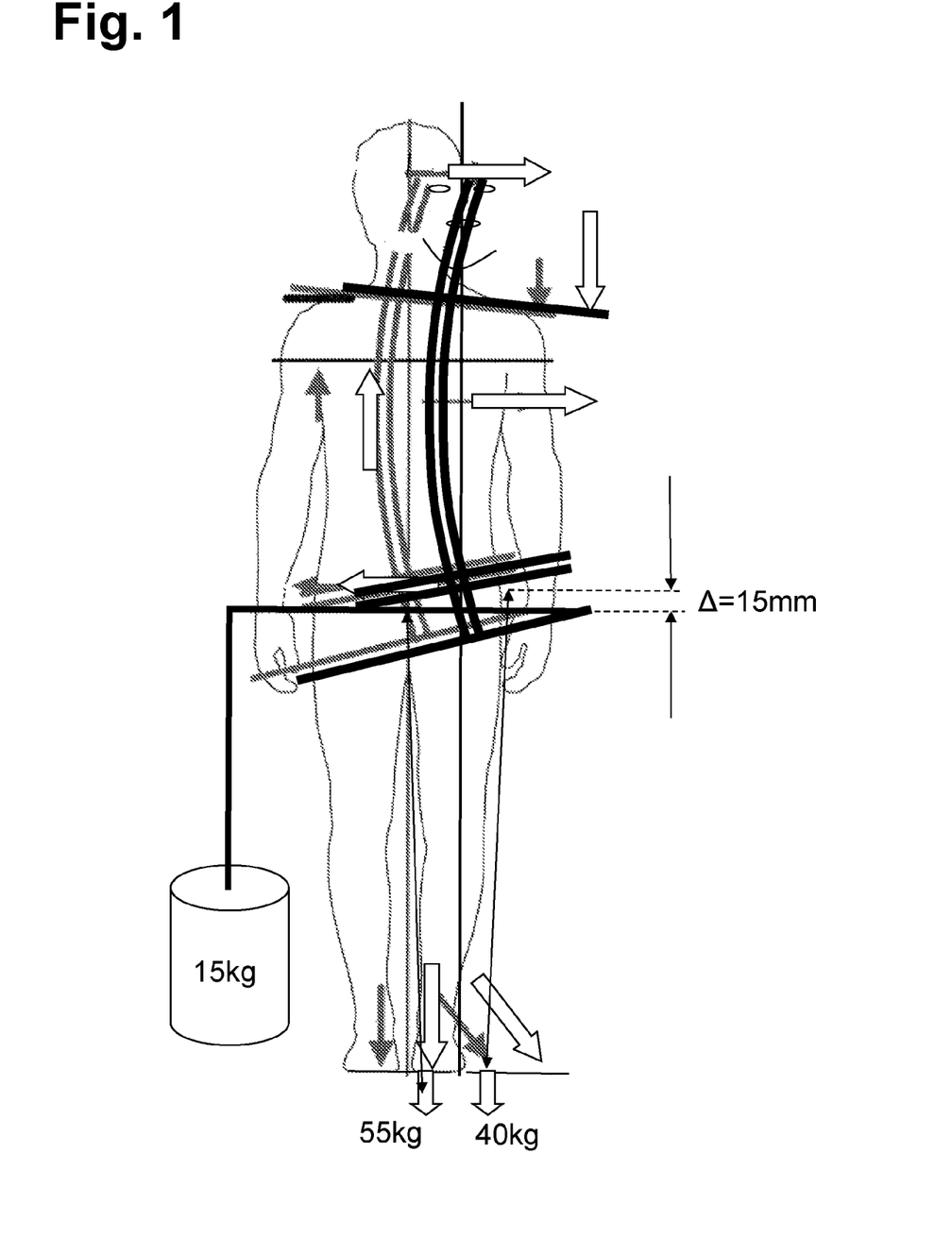
FIG. 1 A man with pelvic obliquity as seen from the front.

FIG. 1 shows the measurement by the example of a standing man who has pelvic obliquity. On the left foot he carries 15 kg less than on the right, which happens more often than one would think. The pelvic obliquity results in his right leg being shorter than his left leg by about 25 mm. Such tension-induced skeletal changes are usually accepted as given length differences, instead of checking for their causes. In most cases the length difference is due to false tensions and is curable by manual therapy for long-term length adjustment.

Although it is the muscles, tendons and ligaments which hold a body together and not the skeleton, only modest attention is paid to the muscle lines. In contrast, bones and joints are only transmission levers for the muscular system. Particularly the muscle tendon insertions are susceptible to pain because they are partly where the force transmission of the body's internal leverage forces takes place. They are located primarily in proximity to the joints, which is why the joints are held responsible for the pain. However, this only identifies the point overload. Information about what is actually inducing the pain is provided by the muscle lines, which have been distorted by the avoidance posture. Only if they are released from their tense position can the skeleton be returned to its optimal, basically symmetric posture.

Figure 2:
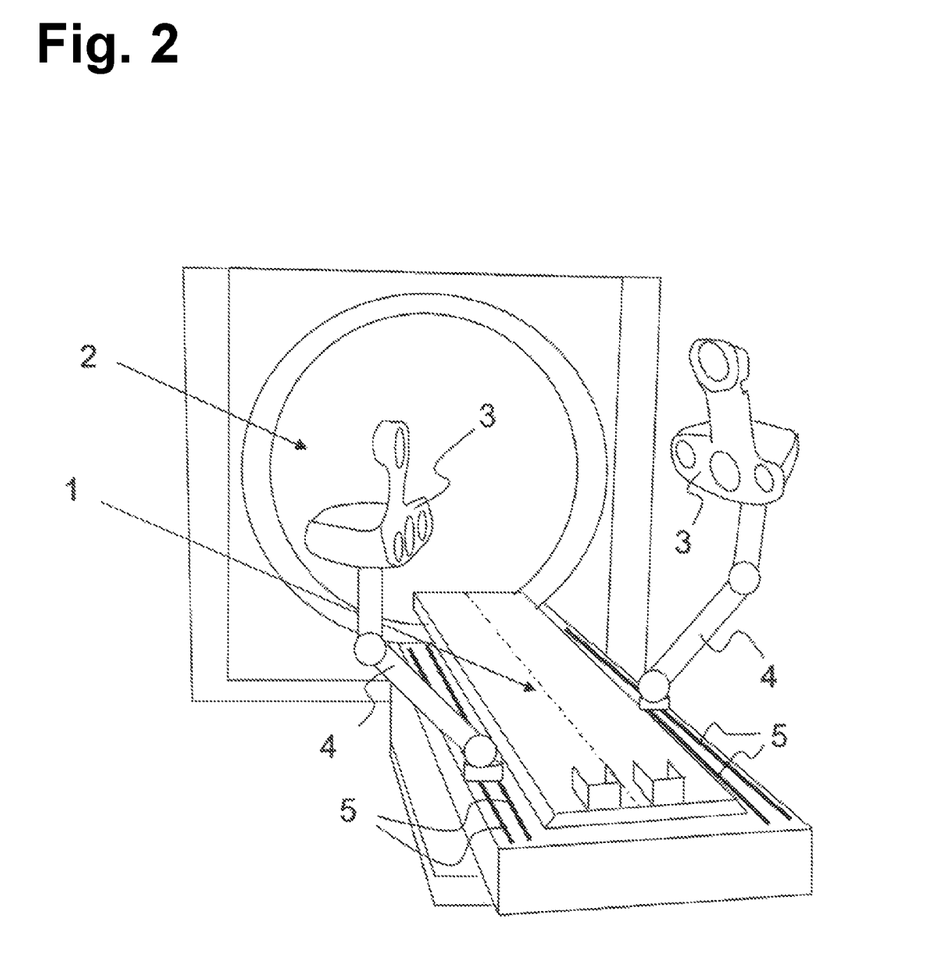
FIG. 2 A patient couch for medical imaging examination devices having a capturing device in the form of 3D scanners.
Figure 3:
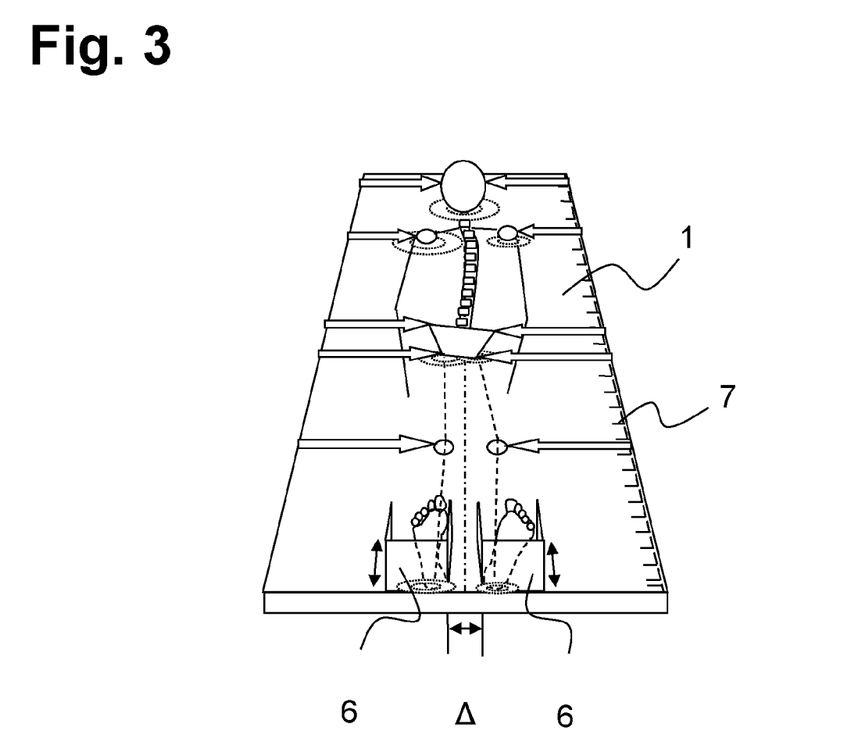
FIG. 3 A patient couch in an inclined plan view as seen from the foot side, having a schematically drawn person lying thereon with the measurement sites for capturing the position of the different body parts.

FIG. 2 shows a patient couch 1 for carrying out radiological medical imaging examinations by means of X-ray, tomography, nuclear magnetic resonance and other imaging methods, which, having a capturing device, is suitable for measuring the position of the individual body parts as well as the local weight load and can even deliver a three-dimensional image of the lying patient. With the imaging method performed in the tube 2, tomographic and other images can be created of a person in lying position. For this purpose, the person lying on the couch 1 is pushed into the tube 2, in which the imaging methods are then applied. However, the exact position of the patient on the couch 1 is previously measured by the capturing device, so as to be comparable to newly measured body positions as a reference later, for example after a therapy. In the example shown, the capturing device includes two laser 3D scanners 3, which each rest on articulated arms 4 which are swivelable in every direction, and the scanners 3 are mounted on the end of said arms so as to swivel in all directions. At the bottom, the arms 4 are guided displaceably along rails 5 longitudinally of the couch 1. Thus, the laser 3D scanners 3 can in any case be brought into an optimal position for scanning a person lying on the couch. Suitable 3D scanners for such applications such as the Go!SCAN 50 scanner from Inspeck Inc., Montreal, Quebec H2X 2V1, Canada, work as described in their EP 1 277 026, that is, they form a self-referencing system and an apparatus for three-dimensional scanning. Such optical 3D sensor technologies enable very high-speed capture of a great amount of data on object areas, so that very high point density is attainable in real time. With a framework for generating highly precise points on the basis of this gigantic amount of data, one ultimately succeeds in representing a body in a photogrammetric manner, so that measurements are capturable thereon. An intelligent measuring process, the data framework, the real-time processing, the calibration and the capture model are the key elements of the technical foundations which ultimately make such high-precision optical 3D measuring systems possible. The recording is made when a patient is resting with his or her feet initially in the footrests 6, as shown in FIG. 3. Said footrests serve the purpose of positioning the feet in lying position as if the patient were standing. In this position the feet are secured with the rests 6, that is, the supporting faces for the feet in both footrests 6 lie in the same plane, because they imitate the floor. One foot may, however, be standing askew in the footrest 6 according to the patient's individual foot position. After all, the goal is to scan the body in lying position as far as possible in the body statics that it would have when standing. Specifically obliquities, rotations of the hip, of the hip joints, the spine and therefore the shoulders and the head are thus to be captured.

Moreover, the couch 1 is equipped with a plurality of pressure sensors, so that the support load can be captured at every site. A suitable flat pressure sensor for this purpose is, for example, the square pressure sensor Interlink FSR406 from Interlink Electronics, Inc., 546 Flynn Road, Camarillo, Calif. 93012, USA. Said pressure sensor FSR406 can measure in the range of about 10 grams to 10 kg of weight, and is 43.7×43.7 mm big and only 0.46 mm high. The active area measures 39.6×39.6 mm. Such square sensors are arranged in a checkered pattern over the entire couch 1. Said pressure sensors act similarly to membrane switches, but unlike conventional switches, they change the resistance upon pressure applied in normal direction. A finger pressure of 10 g to 10 kg on a sensor causes the resistance to drop from about >1 MΩ to about <3 KΩ. The pressure sensors Interlink FSR400 and FSR 400short may also be suitable, only they have a circular sensitive area of 5.08 mm or 5.6 mm in diameter, with a total diameter of 7.62 mm and a height of 0.3 mm. Their sensor area is self-adhesive, so that they are incorporated directly into the layer construction of the couch 1, on which they are covered only by a protective layer on which the patient then effectively lies.

FIG. 3 shows a patient couch 1 in an oblique plan view as seen from the foot side, with a schematically drawn person lying thereon with the measurement sites, indicated by arrows, for capturing the position of the different body parts. On the foot side, one sees both footrests 6, and double arrows show how they can be displaced. The displacement to the left and right is synchronized so that they are always at the same distance from the longitudinal center axis of the couch 1. If a person has, for example, legs of different lengths or legs of supposedly different lengths, after he or she lies down on the couch 1 the footrest 6 is first moved toward the foot of the shorter leg until the foot rests tightly on the supporting face in the footrest 6, as if the person were standing thereon, with his or her natural foot position. Subsequently, the other footrest 6 is pushed to the other foot, until both supporting faces are at the same height and the foot is also lying tightly thereon. In this way, standing on the floor is simulated. The footrests are located at a distance Δ of about 5 cm apart. In this defined foot position, the person will assume an entirely personal position, with a quite typical position of the knee joints and hip joints, the pelvic bone, the spine and shoulder as well as the head. As is shown in the shown example, the body is not lying exactly symmetrically, as in most cases. Here, the pelvic bone is somewhat rotated clockwise in the viewing direction, the spine forms an S and the shoulder is oblique, with the right shoulder lower than the left one. The knees are not located at the same distance from the longitudinal center axis of the couch. It is now a matter of capturing precisely this typical position of this person extremely exactly. For this purpose, in the simplest case the body parts are measured at the arrows shown, that is, the distance from the edge of the couch. A scale 7 on the couch 1 itself can be helpful here. The measuring can be effected mechanically, electromechanically or optically by means of laser distance meters, as will be subsequently shown and described. Moreover, one recognizes in FIG. 3 by the dotted circles of various size below the different support points of the body that said body is lying on the surface of the couch 1 with different weights there. These weights can be measured with pressure sensors, as already mentioned for FIG. 2.

Figure 4:
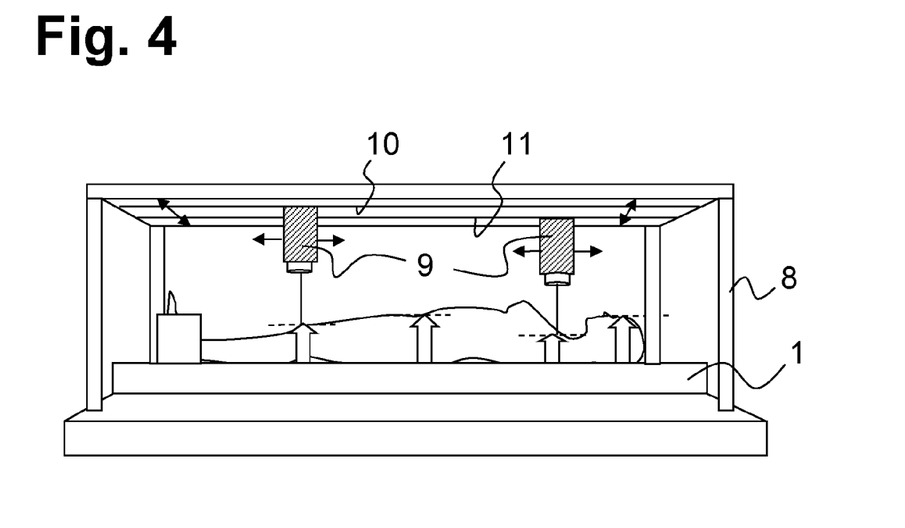
FIG. 4 A patient couch with a person lying thereon as seen from the side, with the body sites whose height is measured starting at the level of the surface of the patient couch.

FIG. 4 shows a patient couch 1 with a person lying thereon as seen from the side, with the body sites whose height is measured starting at the level of the surface of the patient couch. Above the couch 1 here installed is a rack 8 on which at the top two laser distance meters 9 are displaceably mounted along one rail 10,11 in each case, and the rails 10,11 are in turn mounted displaceably on the rack 8 and transversely to the rack 8. The rack 8 can be designed to be set down on the couch 1 so that it can be removed after the measuring is performed, or it is designed to be rollable or slidable over the couch 1. With the distance devices 9 on the rack, the distance from the body parts to be measured can be measured with sufficient precision, contactlessly and quickly, and the data can be read into a computer. A suitable laser distance meter 9 is, for example, the Leica Disto D210 laser distance meter from Leica Geosystems AG in Heerbrugg, Switzerland. This small and handy device measures with a precision of ±1.0 mm and is equipped with a self-timer for precise measurements without moving the device. The data can be read and captured, or read out directly on a computer and can be processed there. Specifically, the distances from the following body parts are measured: from both kneecaps, from both hip joints, from the uppermost points of the pelvic bone, from the shoulders, from the forehead—as shown by arrows. From these distances one can calculate the distances from the surface of the couch 1 to these uppermost points, and together with the horizontally measured distances there results an exact picture of the body position, about any obliquities and rotations. The different supported weights at the heels, the legs, the buttocks and the back and shoulder areas as well as the head indicate the uniformity. Supported weights at these body sites and any asymmetries are recognized by means of pressure sensors in the couch 1, as will be explained more precisely with reference to FIG. 5. Together with the distance data, the body statics can be properly determined, which allows inferences to be drawn about the causes, which can then be treated.

Figure 5:
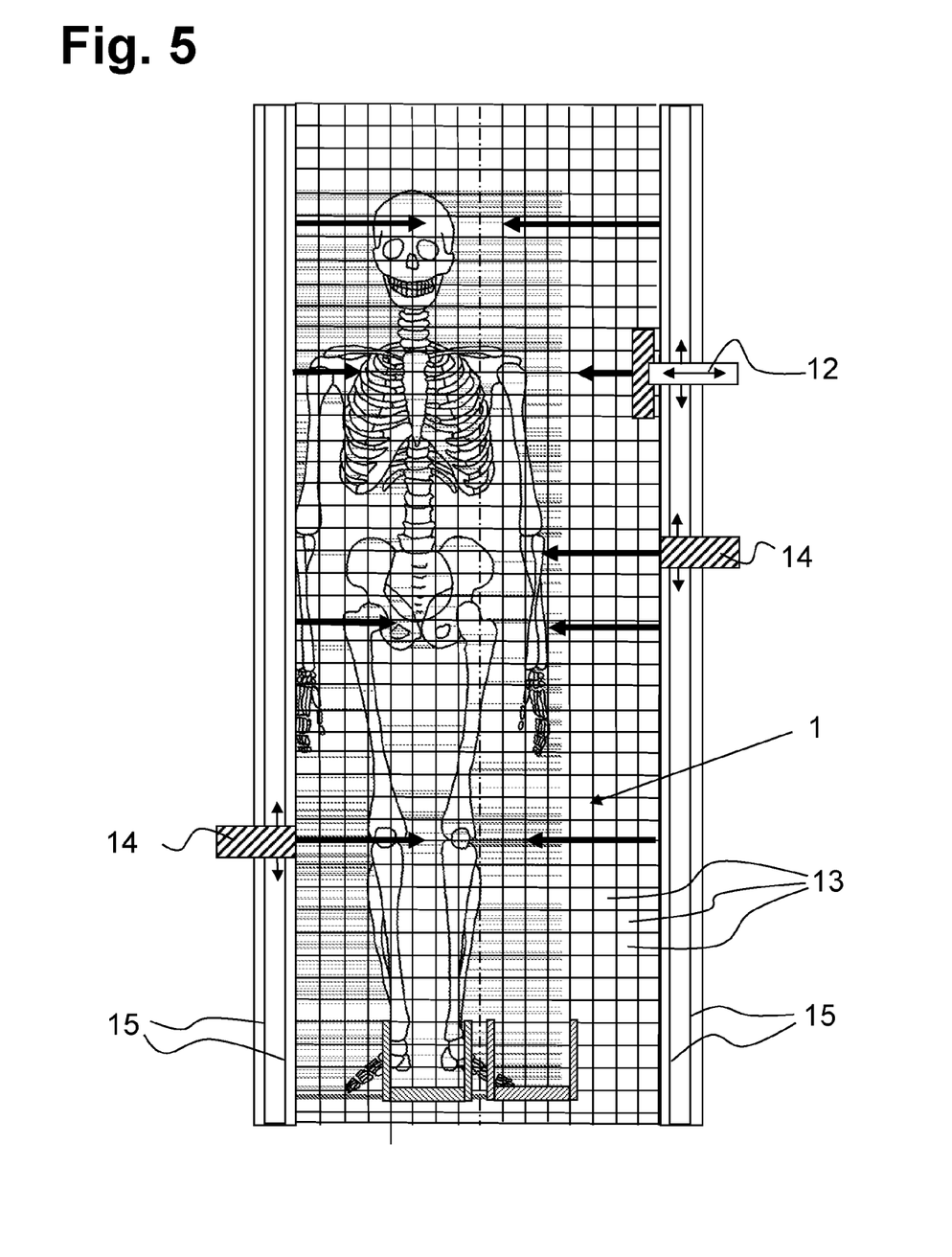
FIG. 5 A patient couch from above, equipped with a plurality of square pressure sensors, and with a skeleton pictured thereon and the sites to be measured thereof, to be captured by means of laser distance meters or mechanical, electrical, hydraulic or pneumatic sliding fixation elements, which are laterally displaceable on rails along the patient couch.

FIG. 5 shows a patient couch which is equipped with a plurality of square pressure sensors 13, and with a skeleton pictured thereon and the sites to be measured thereon, which are measured with lateral laser distance meters 14, which are each displaceable along a rail 15, which extends in the longitudinal direction on each side of the couch. The positions of the head, the shoulder joints, the hip bone, the hip joint and the knee joints are thus relevant here. The feet are placed in the footrests 6 in symmetrical position to the center axis, but not as shown here on the skeleton, but rather such that the soles lie flat against the stop faces, as if the person were standing on his or her feet. The feet may be located at different spreading angles relative to each other, just the way the relevant person effectively and individually stands in the resting state. This foot support proves to be enormously important because it determines the body position above the feet, in lying position as well. The hip joints are rotated accordingly for example, the pelvis likewise, and obliquities at the hip and shoulder as well as lateral deviations from the center axis become visible and measurable. These lateral distances are measured here by means of the two laser-distance meters 14. For the weight supports of the different body parts there are used the pressure sensors 13, which, as already mentioned in connection with FIG. 2 and explicitly shown here, are arranged as square sensors in a checkered pattern over the entire couch 1.

Figure 6:
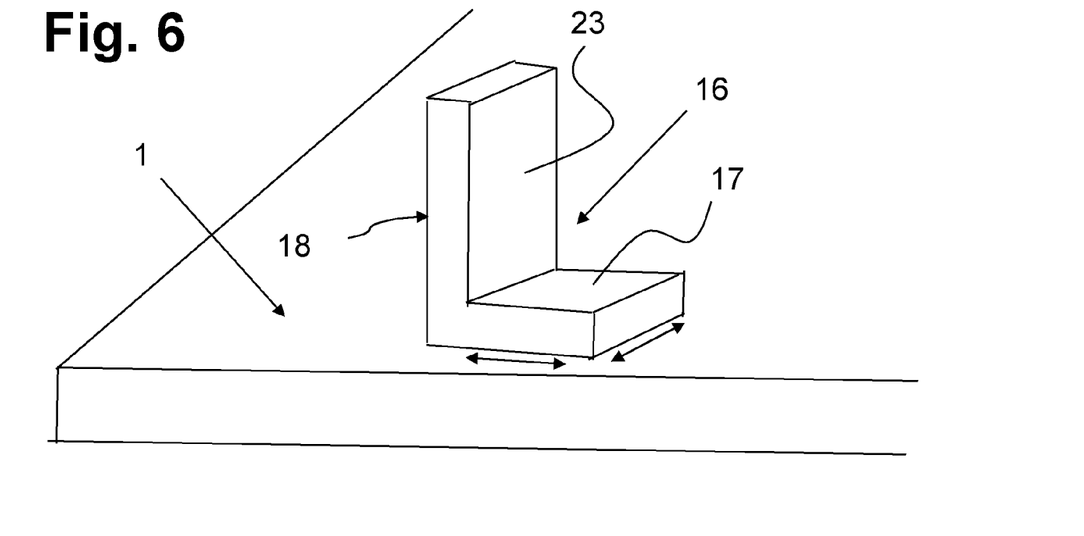
FIG. 6 A corner of the patient couch with a most simple displaceable fixation element pictured thereon, having a vertical stop face to be moved toward a body site for the purpose of measuring its position.

FIG. 6 shows an individual corner of the patient couch 1 with a most simple mechanical capturing apparatus for the body position, without electronic or laser measurement. The figure shows an individual displaceable fixation element 16 with a vertical stop face 18 on the vertical leg 23 to be moved toward a body site for the purpose of measuring its position. These L-shaped fixation elements 16 are displaceable and rotatable in every direction, the desired distances either can be read directly on a coordinate system on the couch, or the respective distances are taken with applied measuring rods and captured. One or more permanent magnets are inserted in the horizontal leg 17 thereof, and the couch contains a magnetizable foil so that the fixation elements 16 apply a sufficient adhesive force in every position, so that a body position can be held for a certain time for all measurements to be taken without haste. As an alternative, the horizontal legs 17 of the fixation elements 16 can also be clamped to the edge region of the couch 1 by means of a quick-release fastener, as with a screw clamp, to prevent displacement when taking the measurements or also during the subsequent imaging method. On an individual patient couch 1 there are, for example, twelve of these fixation elements 16, as can be inferred from FIG. 5, namely, as is shown there, for the following body sites: two fixation elements for the feet, here U-shaped fixation elements as footrests 6, two elements for the hip joints, two for the pelvic bone, two elements for the shoulders and two fixation elements for the two sides of the head, which each consist of an L-shaped molded body. Instead of an L-shaped fixation element it is of course also possible to use a differently shaped fixation element, for instance a cuboid, a rectangular block (cube), or an angle element with a differently shaped foot and a stop face with a different contour.

Figure 7:
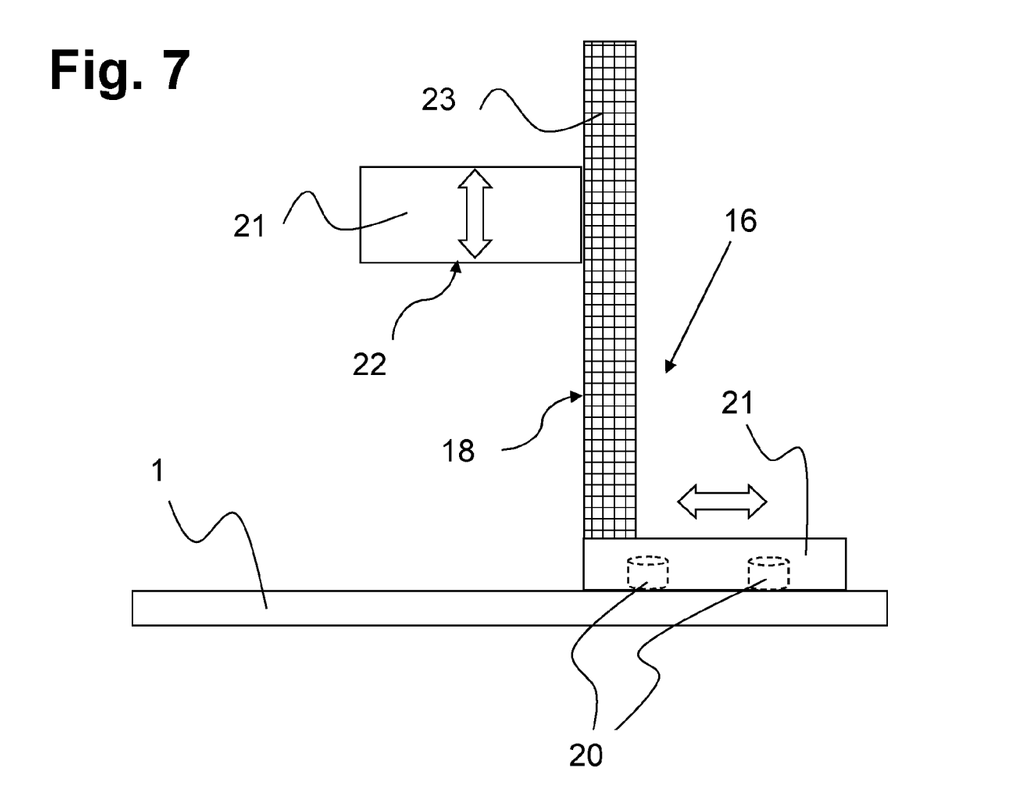
FIG. 7 A patient couch in a side view with a fixation element having a vertical stop face and a horizontally extending, downwardly directed stop face for measuring the height of certain body parts.

FIG. 7 shows a patient couch 1 in a side view with a fixation element 16 having a vertical stop face 18 and additionally a horizontally extending, downwardly directed stop face 19 for measuring the height of certain body parts. By means of this fixation element 16 belonging to the capturing device, the height of the body sites of interest above the plane of the couch 1 can be measured, i.e. the height of the uppermost point of the pelvic bone, the hip joint, the kneecaps, the shoulders as well as the head. In this shown fixation element 16, the permanent magnets 20 are shown in the horizontal leg 17 or foot. The block 21 mounted height-adjustably on the vertical leg serves with its plane underside 22 for measuring the heights of the body parts. For this purpose, the vertical leg 23 is equipped with a scale, so that the height of the downwardly directed stop face 22 is readable directly thereon. In practice, the stop planes are moved from the outside toward the relevant body sites until they are lying tightly against the measurement points. At the top, the fixation element is moved up to the skull cap, and further fixation elements 16 are moved from the outside and then from above toward the shoulder bones. Further fixation elements 16 are moved toward the upper hip bones from the side, i.e. toward the upper end of the pelvic bone from both sides, until said fixation elements 16 reach a stop on the hip bones. Subsequently, the downwardly directed blocks 21, which are attached height-adjustably to said fixation elements, are moved downward until the horizontal, downwardly directed stop faces 22 abut against the upper side of the hip pelvic bones. It is clear that the stop faces do not abut directly against the bones, but lie against the overlying tissue as tightly as possible, so that they virtually feel the bones. Further fixation elements 16 are moved laterally toward the knee joints until they abut against them. And from below, fixation elements in the form of footrests are moved toward the heel bottoms. In this position all fixation elements 6,16 are firmly clamped by clamping means, so that they immovably secure the captured body posture. Now the positions of the fixation elements 16 can be exactly measured, for which different methods are applicable—electronic, electromechanical, by laser or simply by reading. It will be appreciated that the fixation elements 16 can also be configured as slides, which are adapted to be slid horizontally from the couch edge along a guide against the body parts, whereby said sliding can be effected mechanically by hand, electrically, pneumatically or also hydraulically, as is shown on the left shoulder in FIG. 5 with the fixation sliding element 12, which makes the support pressure finely adjustable and repeatable. Said fixation elements, which can be moved out toward the middle of the couch electrically, pneumatically or hydraulically, can be equipped with a laser distance meter, for determining the move-out distance and the position of the fixation elements over the length of the couch.

Figure 8:
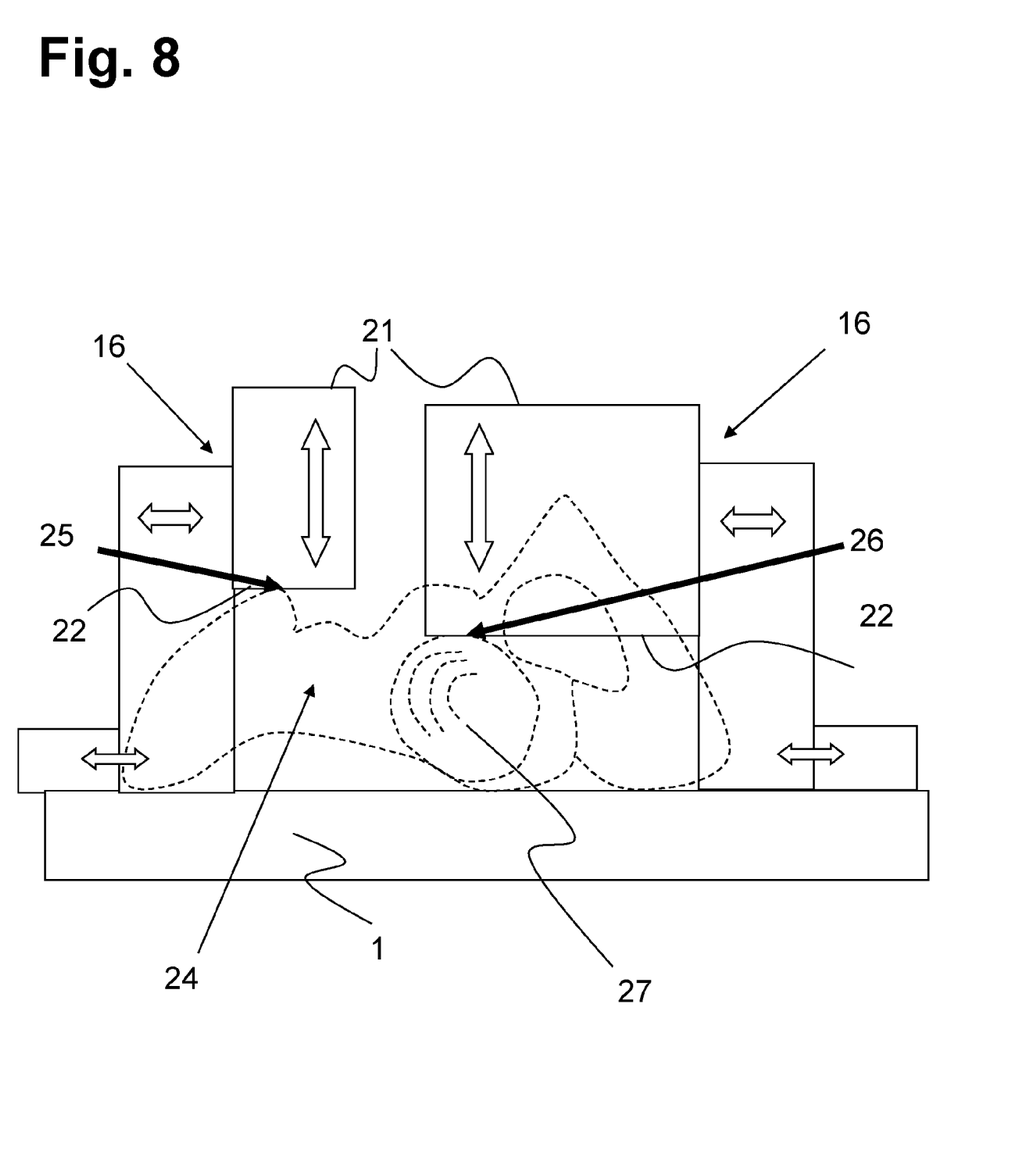
FIG. 8 A patient couch having fixation elements of the capturing device for determining the height of the upper pelvic bone and the hip joint on the basis of a section which shows only the region in which the pelvic bone comes to lie, as seen on the right side of the pelvic bone shown by dashed lines.

FIG. 8 shows a patient couch 1 having fixation elements 16 of the capturing device for determining the height of the upper pelvic bone and the hip joint on the basis of a section which shows only the region in which the pelvic bone 24 shown by dotted lines lies, seen here from its right side, when a person is lying supine on the patient couch 1. The point 25 designates the highest point in the upper region of the pelvic bone, as also shown in FIGS. 5, and 26 indicates the socket 27 for the ball or head on the femur. The levels of these points 25,26 can likewise be established by moving stop faces 22 downward from above. These points or their height above the patient couch 1 must be measured. The capturing device serves this purpose as well, that is, it also permits the body parts protruding upwardly to be measured, specifically, the height of the hip bones on the left and right of the horizontal pelvic bone 24. On the left and right is respectively shown here the fixation element 16 which has a vertically displaceable block 21 having a downwardly directed stop face 22, and these blocks 21 are height-adjustable on the fixation elements 16. One thus moves the fixation elements 16 with the blocks 21 in their uppermost displacement position laterally toward the body of the person who is lying supine on the patient couch 1. Then the blocks 21 are moved down until their undersides 22 abut against the highest elevation of the body part there, for instance of the pelvic bone or of the femoral neck in the case of the socket 27, as is represented in FIG. 8.

Figure 9:
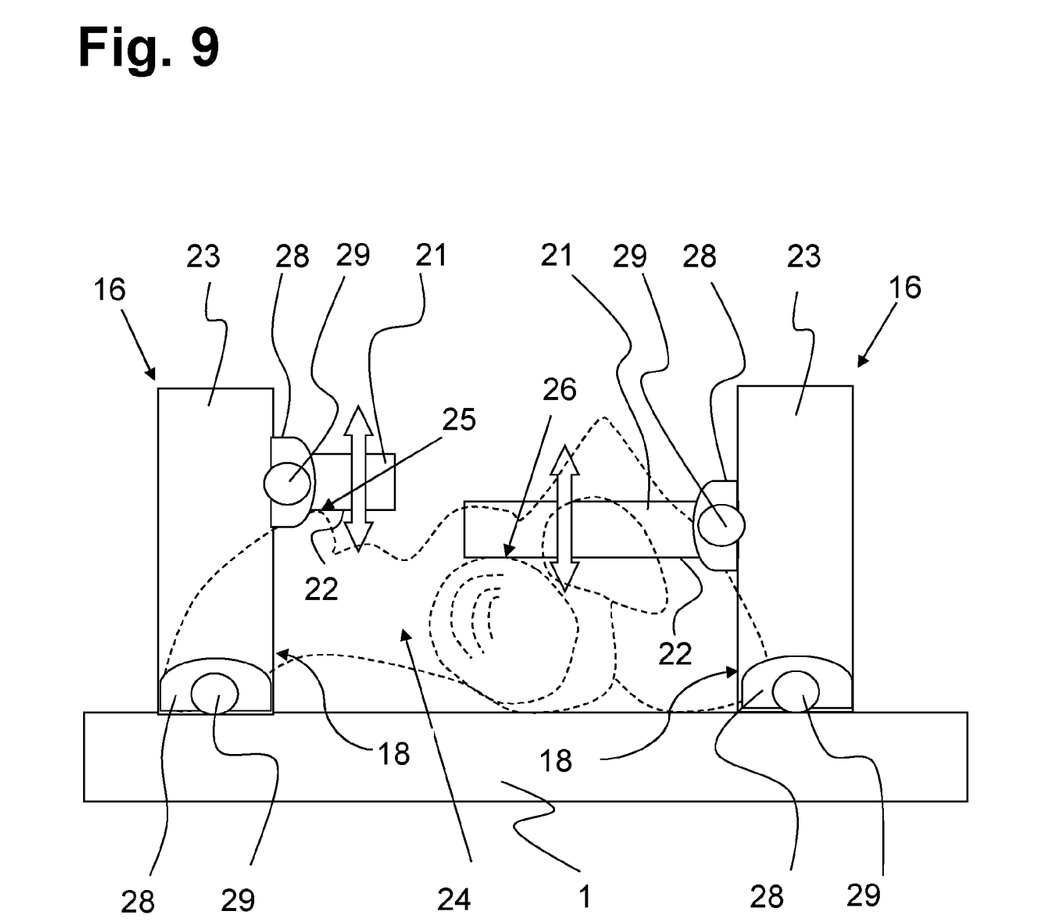
FIG. 9 A patient couch having fixation elements of the capturing device with mouse technology for determining the height of the upper pelvic bone and the hip joint on the basis of a section which shows only the region in which the pelvic bone comes to lie, as seen on the right side of the pelvic bone shown by dashed lines.

FIG. 9 shows a patient couch 1 having fixation elements 16 of the capturing device with electromechanical technology for determining the height of the upper pelvic bone and the hip joint on the basis of a section which shows only the region in which the pelvic bone 24 comes to lie, as seen on the right side of the pelvic bone 24. The fixation elements 16 here are in each case equipped on their underside with a computer mouse 28 with an enclosed track ball 29. Thus, upon displacing the fixation elements 16 on the patient couch 1, which is completely planar for this purpose, the horizontal position can be determined, and captured and displayed as a coordinate in the computer. One thus moves with said fixation elements 16 from a calibrated starting position on the patient couch 1 from the edge region toward the body of the reclining person, until one abuts with the vertical stop face 18 against the correct site of the body. The integrated computer mouse 28 delivers the position via a cable or wirelessly to the appurtenant computer and therefore exactly captures the horizontal position of the stop face 18. The blocks 21 for forming horizontal, downwardly pointing stop faces 22 are guided height-adjustably along rails on the vertical legs 23 of the fixation elements 16. On the contact faces a computer mouse 28 is likewise incorporated in each case, with its enclosed track ball 29 rolling along the stop face 18, that is, the inner vertical face 18 of the fixation element 16, and therefore capturing the height. The uppermost position of the block 21 then forms the calibration position for said computer mouse 28.

It is clear that other methods are also realizable for effectively, exactly measuring the different stop faces. What is important, however, is that these positions of the stop faces on the above-mentioned body sites are indeed captured exactly and reproducibly, be it by optical scanning, by laser distance measuring, by mechanically or electromechanically performed measurements. Only by capturing these body positions can a picture of the effective body position be obtained. This makes it apparent whether or not the body is lying exactly symmetrically with regard to the center axis of the patient couch, whether one leg is shorter than the other, whether an obliquity is present, specifically of the hip or the shoulder, and also whether the hip and shoulder are lying exactly horizontally on the patient couch or whether a rotation is present.

The further findings of the subsequent imaging examination must be urgently interpreted in the light of this body position, so as to be able to more specifically pursue the causes of the findings, in a holistic analysis of the body and its position, not just by analyzing a local, isolated body area.

LIST OF NUMBERS 1 couch
2 tube for imaging method
3 3D scanner
4 arms for 3D scanner
5 rail along couch 1
6 footrests on couch
7 scale on couch
8 rack above couch
9 laser distance meters
10 rail on rack
11 rail on rack
12 electric, pneumatic or hydraulic sliding fixation element
13 pressure sensors
14 lateral laser distance meters
15 rail along couch
16 fixation element
17 horizontal leg of fixation element
18 vertical stop face
19 horizontal stop face
20 permanent magnets
21 height-adjustable block
22 planar underside of block/stop face
23 vertical leg on fixation element
24 pelvic bone
25 highest point on pelvic bone
26 highest point on hip joint
27 socket on pelvic bone
28 computer mouse
29 track ball in computer mouse

The invention claimed is:

1. A patient couch for carrying out radiological medical imaging examinations by means of X-ray, tomography, nuclear magnetic resonance and other imaging methods in which tomographic and other images of a patient in lying position are created, comprising:

a three-dimensional scanner for scanning an entirety of the patient's body and creating a virtual accurate three-dimensional body-image and to represent the body photogrammetrically for measuring the patient's body or certain sites of the patient's body by optical, laser-optical, mechanical or electromechanical means, from which all measurements of interest can be read out, wherein said three-dimensional scanner consists of at least two laser distance meters suitable to measure distances with an accuracy of ±1mm, which are arranged on each side of the patient couch on an arm consisting of two legs and rotatable thereon in every direction, and displaceable along rails installed along the side of the patient couch, so as to be displaceable along the rails in each case and height-adjustable on the rails, further having footrests for positioning soles of the patient's feet on support plates as when standing on vertical supporting faces with natural spreading of the feet, further having measurement means for capturing and measuring at least the distances up to the knee joints, the hip joints, the pelvic bones, the shoulders and the head of the patient such that the patient's back is on the patient couch, and above the patient couch a rack that is adapted to be lifted, rolled or pushed away, and that the patient couch is equipped with pressure sensors for measuring local supported weights of the patient's various supported body sites, for reproducibly capturing position of the patient's skeleton with regard to its center axis as well as any rotations of shoulder and/or hip.

2. The patient couch according to claim 1, wherein the measurement means comprise at least one laser distance meter arranged thereon so as to be longitudinally and transversely displaceable, for determining a maximum height of the kneecaps, the hip joints, both sides of the pelvic bone, the patient's left and right shoulders, and the head of the patient such that the patient's back is laying on the patient couch.

3. The patient couch according to claim 1, wherein beside the three-dimensional scanner, there are a number of mechanical fixation elements which each form a vertical stop face and a planar supporting face and are displaceable and swivelable in every direction on the patient couch in a planar configuration, so that each one of the mechanical fixation elements is movable with its vertical stop face horizontally toward body parts to be measured and in a stop position its position is measurable or readable on a coordinate system printed on the patient couch, as well as a number of such mechanical fixation elements additionally having a height-adjustable block with a downwardly directed, horizontal stop face, so that said vertical stop face is lowerable to certain body parts and a height above a plane of the patient couch is readable on a scale.

4. The patient couch according to claim 3, wherein the number of mechanical fixation elements are fastened laterally to the patient couch and so as to be displaceable along the patient couch, and are adapted to be moved out from there toward a middle of the patient couch mechanically, electrically, hydraulically or pneumatically, for stopping at a certain body site with adjustable contact pressure, and having a laser distance meter for determining a move-out distance and a position of the number of mechanical fixation elements over a length of the patient couch.

5. The patient couch according to claim 3, wherein each mechanical fixation element is an L-shaped molded body whose planar supporting face is displaceable in all directions on the patient couch in the planar configuration and is equipped with at least one permanent magnet in each case, wherein a fixation leg protruding upwardly thereon at right angles is intended to act with its outer face as the vertical stop face for the patient's body parts to be measured, and thereon a downwardly directed stop face is arranged height-adjustably, wherein the fixation leg has a scale for displaying a level of the downwardly directed stop face relative to a surface of the patient couch, and that the patient couch contains an area-covering magnetizable foil, so that the at least one permanent develops adhesive force on the patient couch, and the patient couch further has a coordinate grid on its planar surface, so that a position of the stop face of the mechanical fixation elements is readable directly on said coordinate grid.

6. The patient couch according to claim 1, wherein a number of mechanical fixation elements are coupled with the patient couch which each form a vertical stop face and a planar supporting face and are displaceable and swivelable on the patient couch in a planar configuration in every direction, so that the mechanical fixation elements each are movable with the vertical stop face horizontally toward body parts to be measured and in a stop position its position is measurable electromechanically by the planar supporting face being equipped with a computer mouse integrated therein, wherein a track ball of the computer mouse is rollable on a planar surface of the patient couch, as well as the number of mechanical fixation elements additionally having at least one height-adjustable block with a downwardly directed, horizontal stop face, so that said horizontal stop face is lowerable to certain body parts, and in the at least one height-adjustable block is integrated a computer mouse whose track ball rolls upon vertical displacement of the at least one height-adjustable block on a vertical leg of the number of mechanical fixation elements, for determining a height above the plane of the couch, and that signals of the computer mouse are transmittable via cable or wirelessly to a computer for establishing a horizontal position of the vertical stop face and a height of the horizontal stop face when adjacent to the body of the patient lying with the patient's back on the patient couch.

7. The patient couch according to claim 1, wherein the patient couch is equipped with flat pressure sensors arranged thereon in a checkered layout, for measuring the weight of locally supported body parts of the patient lying on the patient couch, with a resolution of at least 50 mm×50 mm.

8. The patient couch according to claim 1, wherein the three-dimensional scanner offers a resolution of 0.5 mm with a precision of up to 0.1 mm, for scanning parts of 0.3 m to 3 m in size with a tissue resolution of 50 to 150 dpi, and 24-bit colors as well as output formats .dae, fbx, .ma, .obj, .ply, .stl, .txt, .wrl, .x3d, .x3dz, and .zpr, and are thus suitable for self-referencing, three-dimensional scanning of the entirety of the body of the patient lying on the patient couch.

9. The patient couch according to claim 2, wherein the at least two laser distance meters are dust- and splash-proof, and are equipped with an illuminated three-line display and offer a measuring precision of ±1.0mm and storage for ten sets of measurements most recently taken.

* * * * *